(12) United States Patent
Zehner et al.

(10) Patent No.: US 6,777,397 B2
(45) Date of Patent: Aug. 17, 2004

(54) MIXTURES OF FRUCTOSE AND LACTOSE AS A LOW-CALORIE BULK SWEETENER WITH REDUCED GLYCEMIC INDEX

(75) Inventors: Lee R Zehner, Brookeville, MD (US); Warren L. Zehner, Ocean City, NJ (US)

(73) Assignee: Vivalac, Inc., Brookeville, MD (US)

( * ) Notice: Subject to any disclaimer, the term of this patent is extended or adjusted under 35 U.S.C. 154(b) by 0 days.

(21) Appl. No.: 10/233,748

(22) Filed: Sep. 3, 2002

(65) Prior Publication Data

US 2003/0082286 A1 May 1, 2003

Related U.S. Application Data

(63) Continuation of application No. 09/852,462, filed on May 10, 2001, now abandoned.
(60) Provisional application No. 60/279,249, filed on Mar. 28, 2001.

(51) Int. Cl.$^7$ .................. A01N 43/04; A61K 31/715; A23G 3/00
(52) U.S. Cl. ................. 514/53; 514/23; 514/54; 514/60; 426/658; 426/661; 426/804
(58) Field of Search ............... 514/23, 53, 54, 514/60; 426/658, 661, 804, 548

(56) References Cited

FOREIGN PATENT DOCUMENTS

GB             1574848 A   *   9/1980

OTHER PUBLICATIONS

Hyvonen et al., "Examination of Sugars, Sugar Alcohols, and Artificial Sweeteners as Substitutes in Strawberry Jam Product Development", Journal of Food Sciences, 1983, vol. 48, No. 1, pp. 183–192.*

Jana et al., "Sweeteners for Frozen Success—A Review", Australian Journal of Dairy Technology, 1994, vol. 49, No. 2, pp. 98–109.*

* cited by examiner

Primary Examiner—James O. Wilson
Assistant Examiner—Traviss C. McIntosh, III
(74) Attorney, Agent, or Firm—McDermott, Will & Emery

(57) ABSTRACT

Mixtures of fructose and lactose are useful for reducing caloric intake and glycemic index for individuals who are overweight, glucose-impaired, diabetic, or who just consume too large a fraction of their calories from "added sugars". The fructose/lactose sweetener is included in the daily diet as a one-for-one replacement for "added sugars" in various edible formulations without sacrificing quality of taste. Sucrose can be used as a replacement for all or part of the fructose in the claimed sweetener to increase sweetness or improve certain functional properties without substantially changing caloric value. The claimed mixtures of fully-caloric sugars work synergistically to reduce available calories and blood sugar concentration. Specifically, fructose interferes strongly with normal small-intestinal absorption of lactose and interferes moderately with sucrose absorption, while lactose interferes with normal small-intestinal absorption of both sucrose and starch. Unabsorbed di- and oligosaccharides pass into the colon and cause increased growth of healthful bacteria, making the new sweetener useful as a prebiotic. No gastrointestinal symptoms of sugar intolerance were observed when the claimed sugar mixtures were ingested at normal dietary levels.

19 Claims, 5 Drawing Sheets

MIXTURES OF FRUCTOSE AND LACTOSE AS A LOW-CALORIE BULK SWEETENER WITH REDUCED GLYCEMIC INDEX

CROSS-REFERENCE TO RELATED APPLICATIONS

This application claims the benefit of provisional patent application Ser. No. 60/279,249, filed Mar. 28, 2001, and of continuation copending application Ser. No. 09/852,462, now abandoned, filed May 10, 2001, both incorporated herein by reference.

FEDERALLY SPONSORED RESEARCH

Not applicable.

SEQUENCE LISTING OR PROGRAM

Not applicable

BACKGROUND

1. Field of Invention

This invention relates to mixtures of sugars useful for reducing caloric intake and glycemic index 2. Prior Art Americans' rapidly increasing consumption of added sugars over the last fifteen years has contributed significantly to a major public health problem, the reversal of which the US Center for Disease Control and Prevention (Koplan and Fleming, J Am Med Assn, 284, 1696, 2000) has targeted as one of its 'top ten' health goals for the $21^{st}$ century. The problem is the epidemic of obesity in the US. Obesity is defined as a body weight 30% above the ideal body weight Obesity is strongly linked with greater risk of heart disease, high cholesterol and blood pressure, type 2 diabetes, stroke and breast, colon and prostate cancers. A recent study has shown that more than 50% of Americans are overweight, and 22% are obese.

Over the 8-year period from 1991 to 1999, obesity among American adults rose from 12.0% to 18.9%, an increase of 57%. Coincident with the rise in obesity came a 33% increase in type 2 diabetes (from 4.9% to 6.5% overall) In a Reuters news article, dated Jan. 26, 2001, Dr. Ali Mokdad of the CDC's National Center for Chronic Disease Prevention and Health Promotion was quoted as saying, "We've seen a tremendous increase in obesity in the 90's—that's why we're now seeing an increase in diabetes." He went on to say, "Obesity is no longer a cosmetic issue, but a risk factor for serious illness We need to change our behaviors to reduce many of the chronic diseases we are facing, not only diabetes."

The average American now consumes more than 80 grams of added sugars (typically as sucrose, glucose and fructose) each day. Added sugars are those sugars that are incorporated by man into processed foods and beverages, and do not include sugars that are naturally present in the natural and processed foods that we eat. Over the 8-year period from 1991 to 1999, adult consumption of added sugars rose from 70 to 80 grams/day while consumption of fat (and presumably protein) remained fairly constant. The average adult body weight over the same time period increased 2.9 lb, from 166.5 lb to 169.4 lb. We assume a constant level of activity for the adult over the 8-year period. Then, the increased consumption of added sugars (10 grams/day×3.9 kcal/gram=39 kcal/day vs an average 2000-kcal/day diet) alone can account for 3.2 lb, or all of the body weight increase observed over the 8-year span. Clearly, added sugars are important in controlling unwanted weight gain in adults.

The US Department of Agriculture recommends that an adult who eats a 2000-kcal/day healthful diet should try to limit himself or herself to consumption of about 40 grams of added sugars per day, or 8% of total caloric intake. This level of consumption is ½ of the current level of added sugars, with ½ of the associated calories. The subject invention allows one to continue consuming 80 grams of added sugars per day, but with no more than the caloric intake of the USDA-recommended 40 grams per day of added sugars. The subject invention, in addition, allows one to consume the same sugars that have gained acceptability (e.g. safety, quality of taste, ease of use in foods, and low cost) for many decades without exposure to any new or rare carbohydrates, carbohydrate derivatives, rare plant extracts, or artificial sweeteners.

Fructose, lactose and sucrose are widely consumed natural sugars in the American human diet (37, 16 and 81 grams/capita/day, respectively). All are known to be fully caloric (i.e., approximately 4 kcal/gram) when used separately in typical foods. It is known that ingestion of any of the three cited sugars as part of diet does not interfere with absorption of glucose, protein, or lipid from the small intestine. In fact, no report of any interaction of fructose, lactose, or sucrose with other human dietary components to reduce caloric utilization or raise glucose tolerance in animals or man has been reported previously. It is widely known (Wolever, 1995) that fructose has a substantially lower glycemic index (23) than lactose (46), sucrose (61 to 64), glucose (100), or oat starch (100). Because of their low glycemic indexes, fructose and lactose separately have been posed as useful for diabetics (Wolever et al, 1985 and Wolever et al, 1995), but no synergy between the two sugars or with other sugars has previously been disclosed that would suggest lower-than-expected glycemic indices or reduced caloric utilizations.

With the aforementioned facts about the three subject sugars in mind, the literature reveals prior art in the field of carbohydrate utilization. Eleven animal studies conducted over the past eight decades have shown inconsistent results, which bear on the apparent caloric value of lactose. The results from rats and pigs, the only two animals reported, were not always consistent with human results For example, Whittier et al (1935), Tomarelli et al (1960), and Baker et al (1967) studied the effect of lactose (30%, 52%, and 50% of diet, respectively) with glucose in pair-fed and ad libitum diet as the only two sources of carbohydrate in growing rats' diet, as compared to sucrose or glucose in control diet. All three research groups found lower body weight and body fat in the ad libitum-lactose-fed, sacrificed rats. Pair-fed rats showed the same body weight but lower body fat for lactose vs controls (down 38%, 40%, and 48% respectively). Whittier et al confirmed the lower fat weight effect in pigs fed restricted diets including lactose and brewers' yeast and even found increased longevity in rats fed lactose. Tomarelli et al attributed the observed fat-sparing effect of lactose largely to bacterial action of the disaccharide in the cecum. Similar reduced body fat weights were observed in rats fed sorbitol, cellobiose, and raw potato starch (resistant starch), all of which are poorly absorbed carbohydrates that undergo bacterial degradation in the cecum. The authors noted in exploratory experiments the blood glucose levels of rats fed glucose and lactose diets were not significantly different Baker et al found a greater hypolipogenic effect with the β-anomer of lactose than with the α-anomer Février (1969) studied the effect of lactose (30% of diet) with corn starch (32.7% of diet) as the only sources of carbohydrate in ad libitum, pair-fed, and equal-growth diets in growing rats, as compared to a starch (62.7%) control. Ad libitum feeding resulted in a 37% reduction of growth rate and 20% reduction of fat content for the lactose-fed rats. Pair-feeding resulted in a 23% reduction of growth rate and 32% reduction of fat content for the lactose-fed rats. Equalized-growth-feeding resulted in a 12% reduction of fat content for the lactose-fed rats. The author asserted that the cause of the body fat reduction was the lower metabolizable energy of the lactose and a loss of galactose in the urine.

Dalderup et al (1969) reported that adult male rats fed 15 calorie % lactose in potato and bread starch diet over four months excreted a significantly larger amount of feces and formed a larger amount of lactic acid in feces compared with a 15-calorie % glucose group. These two observations support the notion that lactose in rats is not well-absorbed in the small intestine and is fermented in the cecum and/or colon.

Ali and Evans (1971) studied the growth of weanling male rats fed ad libitum "equicaloric" diets containing either 0 or 12% lactose over a six-week period. The basal diet included 30% starch and 30% sucrose. Lactose was added to the basal diet at the expense of part of the sucrose The work was directed to study effects and interactions of dietary lactose and other dietary components on gross body composition in the growing rat, by multi-variable regression analysis. Lactose did not have any effect on diet consumption or body protein vs basal diet The most pronounced effects were those of lactose on body fat (reduced 30%) and on body moisture (increased 11%). Although interactions between lactose and other dietary components (such as calcium, buffering capacity, and EDTA) were noted, the authors did not identify any interactions between lactose and either starch or sucrose.

Two rat and pig studies tangential to the subject of lactose utilization in diets containing starch found other interesting effects of lactose consumption. In growing pigs and rats, Cheeke et al (1973) found that lactose reduced the digestibility of alfalfa fiber and purified cellulose in the cecum and gut. The effect was admittedly counter-intuitive, and the authors offered no rational explanation. Conclusions were based on weight gains only; no determinations of body moisture, minerals, or fat were made. In another publication, Moser et al (1980) studied postweanling rats fed graded diets in which 30% starch was replaced with increasing amounts of lactose up to 30%. A trend toward poorer growth rate was noted as lactose increased in the diet Rats fed 30% lactose had the poorest feed efficiency of all groups. Body fat was not measured, but ash was determined in femurs. Percentage ash increased linearly as lactose increased.

Jin et al (AJAS, 11 (3), 285, 1998) found that weaned pigs fed diets containing lactose (20%) and corn (36.5%) vs sucrose (20%) and corn (36.5%) were completely equivalent after 3 weeks of feeding. Average daily gain and average daily feed intake were the same for both groups Complete body composition analysis was not performed, but clearly there was no sign of an interaction of the starch from corn with lactose or with sucrose.

Jin et al (AJAS, 11 (2), 185, 1998) reported the results of a study to optimize the ratio of lactose to sucrose for weaned pigs fed ad libitum diets containing graded fractions of lactose (20%) at the expense of sucrose (20%) for three weeks. Both diets contained corn (38.5%) as a source of starch. For the third week, there were no differences among the groups with respect to average daily gain (G), average daily feed intake (F), and the ratio F/G. At the end of three weeks, digestibility of nutrients—dry matter, crude fat, and phosphorus—were not influenced by the varying lactose: sucrose ratio On the other hand, pigs fed lactose at 10%, 15%, or 20% showed significantly improved nitrogen digestibility. The authors propose that the improvement in nitrogen digestibility may be due to the high level of lactase enzyme present in the small intestine of the young pig. Clearly the pig handles digestion of lactose more efficiently than the rat The difference between the pig and rat model raises the question of which one has more relevance to man.

In an article published in 1979 by Karimzadegan et al, the relative availability of lactose in rats compared to glucose was determined in bioassays based on weight gain and plasma ketones to be 0.57 and 0.59, which values correspond to a metabolizable energy value for lactose of 2.1 kcal/g The energy value widely accepted in man and reported in a leading lactose-manufacturer's data sheet (Foremost, 1995) is 3.8 kcal/g. The lower energy value for lactose in rats is due to the much lower activity of the lactase enzyme in the small intestine of the postweanling and adult rat Because the dietary lactose cannot be hydrolyzed completely in the small intestine, it passes into the cecum and colon where bacteria degrade it less energy-efficiently to lactic acid, to short chain fatty acids (SCFA's), and to carbon dioxide and hydrogen. In retrospect, it is the low caloric value of lactose that largely accounts for the observed hypolipogenic effect, the lower growth rate, and the poor feed efficiency in rats. A historically unrecognized interaction between lactose and starch may account for part of these effects also.

A number of interferences between sucrose-absorption in vivo and small carbohydrate molecules are known or can be surmised. Sugimoto (1976) claimed the use of maltitol and lactitol for reducing cholesterol levels resulting from sucrose consumption. The claimants elaborated that these two carbohydrate derivatives inhibit the "absorbance" of sucrose in vivo Similarly, Seri et al (1995) claimed the use of a number of pentoses, 2-deoxy-D-galactose, and D-tagatose as anti-hyperglycemic remedies, which work by inhibiting sucrase and maltase, the enzymes responsible for hydrolysis of sucrose and maltose, respectively, prior to absorption of the disaccharides in the small intestine. Although Gray and Ingelfinger (1966) reported inhibition of sucrose hydrolysis in man by galactose, Seri et al (1995) saw no inhibition of rabbit sucrase or maltase by galactose in vitro, and Alpers and Gerber (1971) saw no inhibition of human intestinal sucrase either. Gray and Ingelfinger (1966) concede that the galactose inhibition they observed is likely due to interference with the active absorption of glucose by galactose, since both monosaccharides use the same active transport mechanism Fructose and glucose have been reported to inhibit the hydrolysis of sucrose by human sucrase in vitro (Alpers and Gerber, 1971) No interactions between lactose and sucrose-absorption have been reported previously, to our knowledge.

Other than the Seri et al (1995) claims, only one interference of a small carbohydrate molecule with maltose-absorption in vivo is known to the claimants. Maltose is the predominant disaccharide that forms by α-amylase-catalyzed hydrolysis of starch. The sole product of maltose hydrolysis, glucose, also inhibits the maltase-catalyzed hydrolysis of maltose in vitro (Alpers and Gerber, 1971). Fructose and galactose have no inhibiting effect on maltose hydrolysis in vitro (Alpers and Gerber, 1971). No interactions between lactose and maltose-absorption have been reported previously, to our knowledge Several interferences between lactose-absorption and small carbohydrate molecules in vivo may be suggested in the literature but are not obviously applicable to everyday dietary understanding. Glucose, galactose, and fructose have been reported to competitively inhibit hydrolysis of lactose by human lactase in vitro (Alpers and Gerber, 1971). Sucrose and maltose have no inhibiting effect on lactose hydrolysis in vitro (Alpers and Gerber, 1971) Based on the abovementioned in vitro interferences alone, it would not be obvious to one skilled in the art that lactose absorption in human small intestine would be strongly inhibited (enough for lactose to interfere with sucrose and maltose absorption) by glucose, galactose, and fructose, all of which are absorbed rapidly (glucose and galactose are absorbed approximately 1.7 and 1.2 times as fast as fructose) in the human small intestine (Gray and Ingelfinger, 1966).

Wolever et al (1985) compared the effect of added lactose (25 g) with added sucrose (25 g), fructose (25 g), and glucose (25 g) to porridge oats (21.5 g) on the acute blood glucose responses of six diabetic volunteers, directly after their normal use of insulin or oral diabetes agents The calculated glycemic indices (GI's) for the respective sugars vs glucose (GI=100) were 48, 63, 24, and 90; all, except glucose, agree well with GI's reported for normal subjects The subjects considered the sucrose and fructose sweeter than lactose and glucose, but tended to prefer the taste of the less sweet meals. No symptoms suggestive of lactose malabsorption were observed The authors suggested that the long-term effects of lactose on blood lipids need further study No interaction of added lactose, or of any other added sugar, with starch was reported Gannon et al (1986) compared untreated diabetics' plasma glucose and serum insulin responses for sucrose, glucose, fructose, glucose+fructose, or lactose in portions that contained 50 g of total carbohydrate, both in natural foods, like fruits and milk products, and as pure substances The glucose responses were essentially the same whether the carbohydrates were given in pure form or in naturally occurring food. In general, the blood glucose areas under the curve (AUC) could be predicted by the known metabolism of the constituent monosaccharides. Insulin responses, however, were not always predictable, particularly in the case of milk, which contains a powerful insulin secretagogue.

Food articles tested by Gannon et al included ice cream, which contained 34 g sucrose and 16 g lactose (along with 7.4 g protein and 13.2 g fat). In summary, the authors stated, ". . . the single meal plasma glucose response is characteristic for each type of mono- or disaccharide in a food, and is little influenced by other constituents present in these meals." The claimants disagree strongly with this generalization and feel that Gannon et al missed the interaction of lactose and sucrose to reduce plasma blood glucose in ice cream perhaps because the diabetic subjects were not allowed to take insulin or diabetes drugs prior to testing; consequently, the 50-g carbohydrate dose was too large for the AUC to respond in a linear manner to changes in glucose absorption. The GI's that Gannon et al found were not consistent with those from Wolever et al (1985). For example, Gannon et al found GI values for sucrose, fructose, and lactose of 43, 6, and 32, compared with 63, 24, and 48 from Wolever. The latter Wolever values are well-known and widely accepted by other researchers

OBJECTS AND ADVANTAGES

The object of this invention is to provide mixtures of sugars of reduced caloric value compared to prior art sweeteners.

Another object of this invention is to provide mixtures of sugars of reduced glycemic index compared to prior art sweeteners.

Another object of this invention is to provide mixtures of sugars of reduced caloric value with the same sweetness level as sucrose Another object of this invention is to provide mixtures of sugars of reduced caloric value with the same quality of taste and mouthfeel as sucrose.

Another object of this invention is to provide mixtures of sugars of reduced caloric value without aftertaste Another object of this invention is to provide mixtures of sugars of reduced caloric value with thermal stability in baking and cooking similar to that of sucrose.

Another object of this invention is to provide mixtures of sugars of reduced caloric value having duration of sweetness similar to that of sucrose.

Another object of this invention is to provide mixtures of sugars of reduced caloric value which offer the health benefits of dietary fiber.

It is an object of this invention to provide a healthful alternative to so-called "added" sugars that allows anyone to reduce caloric consumption from these sugars to a level acceptable to dietary experts without subjecting one to the potential health risk of a new high-intensity sweetener or rare carbohydrate/carbohydrate derivative.

It is a further object of this invention to provide an alternative sweetener that does not force one to change his or her standards for sweetness or sensory acceptance or to change household food processing to adapt to the physical properties of a sweetener other than the ones he or she has used over a lifetime.

It is a further object of this invention to provide an acceptable sweetener which will help to limit caloric intake for the overweight and obese.

It is a further object of this invention to provide an alternative sweetener to pre-diabetics and diabetics that will reduce postprandial blood glucose levels and ultimately reduce glycosylated hemoglobin levels.

It is a further object of this invention to provide a mild prebiotic that will encourage the growth of beneficial bacteria in the colon, such as varieties of lactobacillus.

A final object of this invention is to provide mixtures of sugars of reduced caloric value which are inexpensive, simple to manufacture, and without adverse effects on the environment The benefits of the new sweetener are reduced caloric intake, reduced glycemic index, same sweetness level as sucrose, high quality of taste and mouthfeel like those of sucrose, no aftertaste, thermal stability in baking and cooking, and normal longevity of sweetness as perceived with sucrose The cost of producing the new sweetener will be fully acceptable to the marketplace because all of the ingredients are inexpensive articles of commerce. In addition, because of the incomplete absorption of the component sugars in the small intestine, the sugars and oligosaccharides resulting from incomplete hydrolysis of starch which pass to the colon and are microbially digested act like dietary fiber and offer the well-known health benefits of soluble and insoluble fiber

SUMMARY

Useful mixtures of sugars disclosed in this application include the mixtures of sugars comprising in percent by weight of the mixture of sugars: lactose 10 to 80, and a mixture of fructose and sucrose, 20 to 90, wherein the mixture of fructose and sucrose consists of in percent by weight of the mixture of fructose and sucrose, sucrose 0 to 100 and fructose 0 to 100, excluding the following mixtures, in percent by weight of the mixture of sugars, lactose 75, sucrose 25, fructose 0; and lactose 50, sucrose 50, fructose 0; and lactose 40, sucrose 60, fructose 0; and lactose 25, sucrose 75, fructose 0.

The apparent caloric values we found for the fructose-lactose, sucrose-lactose, fructose-sucrose, and fructose-lactose-sucrose mixtures are between 1.7 and 2.7 kcal/g, dropping as low as 0.8 kcal/g when the claimed sweetener is used in combination with starch Daily per capita consumption of added sucrose and various corn syrups is approximately 80 g/day (320 kcal/day or 16% of daily caloric intake) in the United States The US Department of Agriculture recommends daily consumption of no more than 40 g of sugars (160 kcal/day or 8% of daily caloric intake) Because of the threshold limit for lactose consumption of 12 g/day in those who are lactose intolerant, we have found that a mixture of 12 g lactose, 12 g fructose, with 24 g sucrose is useful for lactose-intolerants who consume up to 48 g sucrose daily and who wish to reduce caloric consumption without exceeding the daily threshold for lactose or the USDA recommendation for daily caloric intake of added sugars The estimated caloric value for such a mixture is 1.9 kcal/g while the level of sweetness (vs sucrose) is 96%. Those who are lactose-tolerant will find the above mixture of sugars, among others described in the examples, allows them to continue to consume 80 g/day of added sugars while holding the caloric intake from added sugars to 7.6% or less of total daily intake. Similar mixtures of fructose and lactose, with or without sucrose show utility in lowering the postprandial plasma glucose maximum and area under the curve (AUC) for plasma glucose concentration plotted against time for diabetics and pre-diabetics. Other mixtures of fructose, lactose, and sucrose may be used to meet the needs of consumers who prefer less sweetness or a further reduced caloric intake.

DRAWINGS

REFERENCE NUMERALS

Not applicable

DETAILED DESCRIPTION

Figure 1:
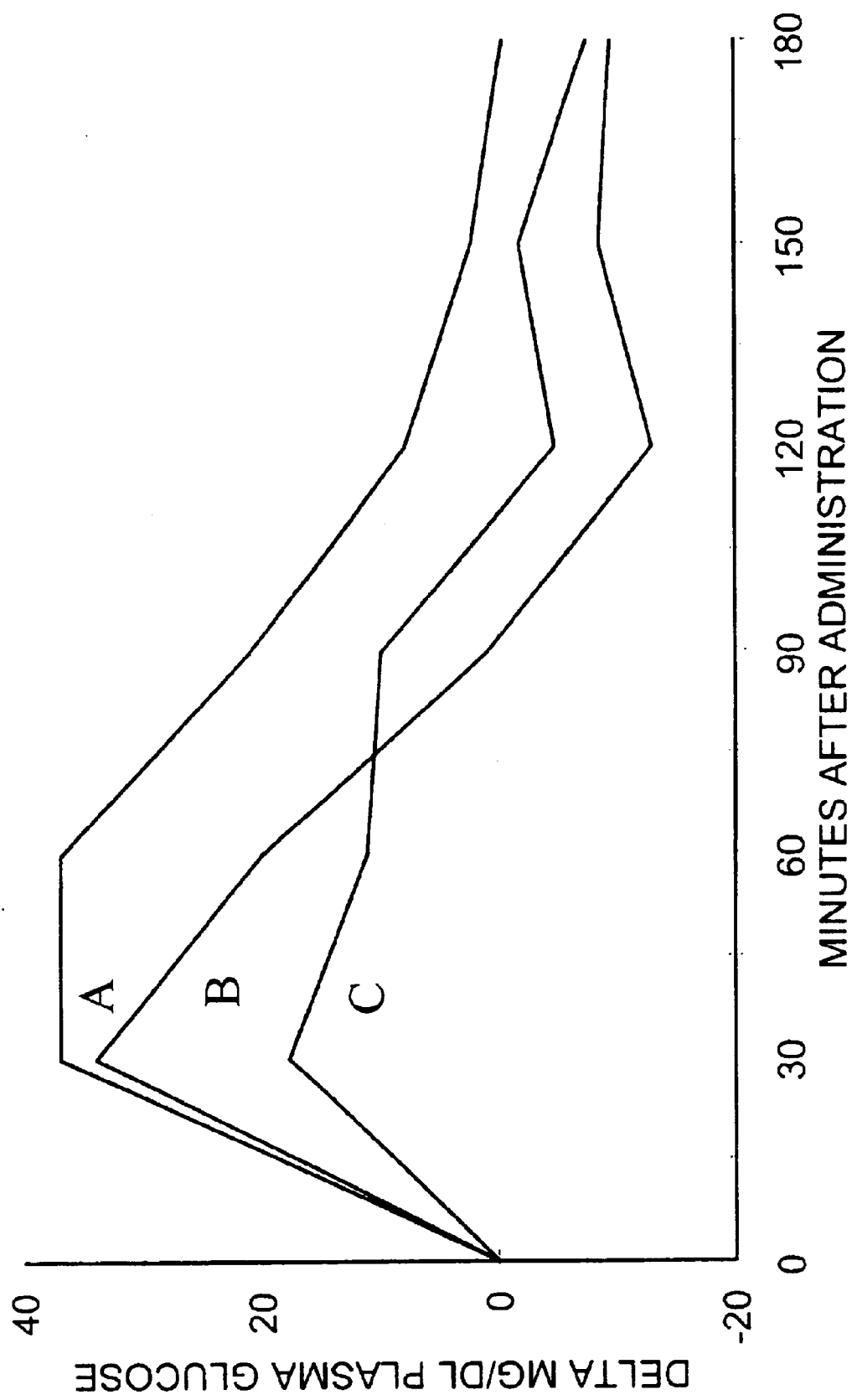
FIG. 1 shows the effects of ingestion of various mixtures of sugars in oatmeal on plasma glucose levels.

In this patent application, each of the following terms has the indicated meaning. "Glycemic index" is the ratio of the area under the plasma glucose curve vs time (AUC) for 50 grams of ingested carbohydrate in question divided by the AUC for 50 grams of glucose times 100. "Percent by weight" means the percent by weight of each material with the indicated composition; in the case of α-lactose, calculations are stated based on the weight of the monohydrate, as available commercially; all other sugar compositions, including fructose, sucrose, and β-lactose, are calculated based on the weight of each commercially-available, anhydrous sugar The term "sweetener" means a mixture of edible sugars The mixtures of edible sugars of this invention comprise the following three: fructose, lactose, and sucrose. Specific useful combinations are fructose and lactose, sucrose and lactose, and fructose, lactose, and sucrose. The mixture of sugars comprise, lactose 10 percent by weight to 80 percent by weight, and a combination of fructose and sucrose, 20 percent by weight to 90 percent by weight, wherein the combination of fructose and sucrose consists of sucrose 0 percent by weight to 100 percent by weight and fructose 0 percent by weight to 100 percent by weight The specified mixtures of fully-caloric sugars unexpectedly have been found to work synergistically to reduce available calories and postprandial blood sugar concentration, without gastrointestinal symptoms of sugar intolerance.

The mechanism of this desirable synergistic interaction between the sugars is not known. Without wishing to be held to this explanation, however, the inventors of the present application suggest the following explanation of the discovery It appears fructose interferes strongly with normal small-intestinal absorption of lactose and moderately with sucrose absorption, while lactose interferes with normal small-intestinal absorption of both sucrose and starch. The unabsorbed sugars, including α-dextrins and maltose from co-nutrient starch, pass into the colon where they are completely degraded microbially to non-caloric (to the host) biomass and short chain fatty acids (SCFA's) The latter are absorbed into the bloodstream and provide the host with a limited amount of energy.

Lactose may be used in the form of the α-lactose monohydrate or the anhydrous β-anomer. Fructose may be used as the crystalline form or as aqueous syrup for preparation of spray-dried or syrup products. Sucrose may be used as the pure granulated form, confectioner's sugar, the various degrees of brown sugar, or even as molasses for preparation of syrups. Use of brown sugar as an ingredient in the subject mixture allows the preparation of a caramelized sweetener, which is useful in baking.

The sweetener in solid form may be used as a physical mixture of the crystalline sugars of similar crystal size, as a co-crystallized mixture of sugars, or as a spray-dried solid, for example The sweetener may also be used in aqueous syrup form or in dilute aqueous/alcoholic solutions.

The subject sweetener may also employ common food-grade additives and processing aids that keep the mixture dry and flowable. Sweeteners such as aspartame, 1,6-dichloro-1,6-dideoxy-β-D-fructofuranosyl-4-chloro-4-deoxy-α-D-galactopyranoside, acesulfame-K, saccharin, stevioside, thaumatin, alitame, or N-[N-(3,3-dimethylbutyl)-L-α-aspartyl]-L-phenylalanine-1-methyl ester may be employed to increase the sweetness whenever desired. On the other hand, diluents to reduce sweetness while maintaining low caloric value may be employed. Such diluents include maltodextrins, polydextrose, and cellulose.

For the purpose of this patent application, we refer to the combination of the subject sweetener and any of the following list of edible foodstuffs as a sweetened edible formulation. The subject sweetener is useful for sweetening a large number of edible foodstuffs, including processed beverages such as carbonated and non-carbonated soft drinks, fruit drinks, flavored dairy drinks, vegetable juices, egg nogs, wines, liqueurs, coffee, or tea; including processed foods such as sweet baked goods, dairy desserts, breakfast cereals, hard candies, meats processed with sweet liquors, custards, salad dressings, vegetable pastes and sauces, condiments such as catsup and salsa, pickles and relishes, ice creams, sherbets and flavored ices, ice milk products, icings, confections and confection toppings, syrups and flavors, jams and jellies, cake and pastry mixes, and pie fillings; including functional/nutritional foods such as sports drinks, nutrition bars, nutrition powders and gels, probiotic yogurt and cultured dairy foods, and nutritional supplements; and is useful as a tabletop sweetener. Other edible formulations that may be sweetened by the subject sweetener include pharmaceutical and nutraceutical products requiring a sweetener/excipient and pet foods In using the sweetener of this invention, it is incorporated in the material to be sweetened in the amount required to attain the desired level of sweetness. It is obvious that there is nothing critical about the concentration of sweetening agent or mode of mixing which is used. It is simply a matter of attaining a desired sweetness level appropriate to the material in question.

Conclusions, Ramifications, and Scope

It will be apparent to those skilled in the art that the examples and embodiments described herein are by way of illustration and not of limitation, and that other examples may be used without departing from the spirit and scope of the present invention, as set forth in the appended claims

EXAMPLES

The present invention will hereinafter be described in more detail by the following examples It should, however, be borne in mind that this invention is not limited solely to these examples possible after the time 0 blood sample was obtained Subsequent blood samples were taken at 30, 60, 90, 120, 150, and 180 minutes, and plasma glucose measurements were recorded in units of mg/dL immediately each time using a hand-held glucometer (At.Last model, Amira Medical, Scotts Valley, Calif. 95066). The subject abstained from food and remained sedentary during the 3-hour test. Clinical observations were noted and recorded continuously.

The subject was tested with duplicate 51:24, 34:16, and 17:8 g sucrose/g starch OTT's to assure linearity of the plasma glucose response as area under the curve (AUC) vs dose. The dose response for this subject was linear between 0 and 50 g total carbohydrate; thus, all subsequent testing with this subject was done with 50 g total carbohydrate.

The $\alpha$-lactose monohydrate (Wisconsin Dairies), sucrose (Safeway Inc.), fructose (A E Staley), porridge oats (57% starch, Quaker Instant Oatmeal), and deionized water (½ cup) were heated together in a microwave oven for 1.5 minutes with stirring, 10 minutes prior to ingestion In Table 1, LA=lactose•H2O, SU=sucrose, FR=fructose, ST=oat starch=(0.95×maltose). N is the number of times a mixture was tested. AUC is the area under the curve for $\Delta$ plasma glucose concentration vs time in units of mg-min/dL. AUC theoretical was calculated based on the known AUC for SU/ST (3155 mg-min/dL) for the test subject and the GI values of 46, 64, 23, and 100 for LA, SU, FR, and ST, respectively AUC theoretical is free of any sugar interactions since there is no known interaction between SU and ST. AUC actual was determined experimentally for the mixture of sugars and includes all of the sugar interactions, if any. The ratio, AUC actual/AUC theoretical, gives a measure of the degree of interaction(s) described in the first column, and $P \leq 0.05$ indicates that the effect is significant, per the student's t test.

TABLE 1

Interferences with Small-intestinal Absorption of Common Sugars and Starch

| Interactions | Lactose grams | Sucrose grams | Fructose grams | Oat Starch grams | N = | AUC theoretical mg-min/dL glucose | AUC actual mg-min/dL glucose | AUC actual AUC theoretical | P |
|---|---|---|---|---|---|---|---|---|---|
| LA × ST | 25.0 | 0.0 | 0.0 | 25.0 | 2 | 3044 | 2295 | 0.75 | 0.02 |
| SU × ST | 0.0 | 34.0 | 0.0 | 16.0 | 3 | 3155 | 3155 | 1.00 | 0.50 |
| FR × ST | 0.0 | 0.0 | 34.0 | 16.0 | 2 | 1983 | 1755 | 0.89 | 0.24 |
| FR × SU | 0.0 | 17.0 | 17.0 | 16.0 | 2 | 2569 | 1965 | 0.76 | 0.04 |
| FR × LA, LA × ST | 8.5 | 0.0 | 25.5 | 16.0 | 2 | 2136 | 1350 | 0.63 | 0.01 |
| LA × ST, LA × SU | 14.0 | 20.0 | 0.0 | 16.0 | 2 | 2918 | 1763 | 0.60 | 0.05 |
| LA × ST, LA × SU | 17.0 | 17.0 | 0.0 | 16.0 | 2 | 2877 | 1613 | 0.56 | 0.05 |
| LA × ST, LA × SU | 20.0 | 14.0 | 0.0 | 16.0 | 2 | 2821 | 1877 | 0.67 | 0.01 |
| LA × ST, LA × SU | 27.2 | 6.8 | 0.0 | 16.0 | 2 | 2709 | 1872 | 0.69 | 0.05 |
| All Interactions | 8.5 | 17.0 | 8.5 | 16.0 | 4 | 2723 | 1002 | 0.37 | 0.0004 |
| Calculated | 12.75 | 8.5 | 12.75 | 16.0 | N/A | 2500 | 580 | 0.23 | N/A |

Example 1

Interactions of Lactose, Sucrose, Fructose and $\alpha$-Dextrins (Maltose) in the Small Intestine The test subject (Subject #1) was a 54-year-old Caucasian male in good health, with a body mass index (BMI) equal to 28.6 kg/M². The subject was required to exercise moderately at least 30 minutes each day before testing, sleep at least 7 hours the previous night, and fast for no less than 12 hours prior to oral tolerance testing (OTT) early the next morning. Water was restricted 1.5 hours prior to testing, and only small sips of water were allowed infrequently during OTT The test article, described below, was ingested as quickly as The testing of the four carbohydrates was performed in order to learn which of the sugars interact in the small intestine to enhance or inhibit the absorption of others. None of these carbohydrates is known to inhibit the $\alpha$-amylase-catalyzed hydrolysis, which converts starch into maltose (~75%) and $\alpha$-dextrins (~25%). Consequently, starch and $\alpha$-dextrins/maltose may be treated as equivalents for the purpose of the following analysis The results are summarized in Table 1. There were no significant interactions between sucrose and $\alpha$-dextrins (and maltose) and no significant interactions between fructose and $\alpha$-dextrins (and maltose), resulting in unchanged actual conversions to plasma glucose vs theoretical AUC. Table 1 shows four significant interferences.

1) Lactose and α-dextrins (and/or maltose) interact to reduce the expected conversion of 50 grams of carbohydrate into plasma glucose.
2) Fructose and sucrose interact to reduce the expected conversion of 50 grams of carbohydrate into plasma glucose.
3) Lactose and sucrose interact strongly to reduce the expected conversion of 50 grams of carbohydrate into plasma glucose
4) Fructose and lactose interact very strongly to reduce the expected conversion of 50 grams of carbohydrate into plasma glucose.

The mechanisms of these desirable synergistic interactions between the sugars are not known. Without wishing to be held to this explanation, however, the inventors of the present application suggest the following explanation of the discovery. Our results show for the first time that lactose significantly interferes with α-dextrins (and/or maltose) absorption, and not vice versa, since it is known from the literature that maltose (and presumably α-dextrins) does not inhibit lactose hydrolysis, the rate-limiting step for lactose absorption. It is likely that this new interference results from lactose inhibition of isomaltase and/or maltase, the enzymes that catalyze the hydrolysis of α-dextrins and maltose, respectively, to glucose.

Our results show that fructose interferes with sucrose absorption, a result that confirms the in vitro inhibition of human sucrase by fructose (Alpers and Gerber, 1971). The presence of sucrose or its hydrolysis products does not inhibit the facilitated diffusion rate of fructose (Gray and Ingelfinger, 1966).

The results from the lactose/fructose/starch and lactose/sucrose/fructose/starch mixtures confirm the newly found lactose interference with starch absorption while showing a further strong interference between fructose and lactose. As it is known that lactose does not inhibit the absorption of fructose, we can only conclude that this strong effect is a manifestation of the inhibition of human lactose hydrolysis by fructose, previously observed in vitro. The effect we observe in vivo is surprisingly strong in light of the fact that fructose is absorbed in the small intestine so rapidly. We believe that the inhibiting effect of fructose on lactase is only effected in the proximal jejunum, where the concentration of lactase in the intestinal mucosa is high. By the time the fructose is fully absorbed, most of the lactose in the bolus has made it through to the ileum where the mucosal concentration of lactase approaches zero (Gudmand-Høyer et al, Adv Nutr Res, 6, 233–69, 1984). This scenario practically assures that lactose, along with unabsorbed sucrose and α-dextrins (and/or maltose), is degraded microbially in the colon, with consequent lower-energy and prebiotic benefits for the sweetener The results from the four lactose/sucrose/starch tests in Table 1 show another new and strongly negative interaction between lactose and sucrose, while confirming the weaker lactose interference with α-dextrins (and/or maltose) absorption. The negative lactose and sucrose interaction can only be due to lactose inhibition of sucrase or to inhibition of glucose and/or fructose absorption, since it is already known that sucrose is not an inhibitor of human lactase in vitro Further, no disaccharide is known to inhibit the absorption of an actively transported or facilitatively diffused monosaccharide like glucose or fructose, respectively. Consequently, we believe we have identified a new inhibition of the sucrase enzyme by lactose. It is also probable that lactose inhibits the closely associated enzyme, isomaltase, responsible for hydrolysis of α-dextrins to glucose Often, an inhibitor of sucrase is also an inhibitor of isomaltase.

As the AUC actual/AUC theoretical ratio approaches zero, caloric value of the sweetener approaches some lower limit below 1 calorie. The test designated "All Interactions" in Table 1 gave an AUC actual/AUC theoretical ratio of 0.37, i.e., only ⅜ of the 50 g carbohydrates or 18.5 g is absorbed from the small intestine into the bloodstream and converted to plasma glucose. The remaining 31.5 g, including ~⅓ of the α-dextrins (and/or maltose) from the oat starch, passed into the colon without any gastrointestinal effects beyond a brief period of mild rumblings and slight fullness in the GI system. The key interferences in this example were fructose/lactose, lactose/sucrose, fructose/sucrose, and lactose/α-dextrins (and/or maltose). The results presented in Table 1 for the "calculated" test show a near-optimal case calculated from a multi-variable regression analysis and have not been confirmed experimentally. In this case, the four sugars interfere so extensively with each other that only a quarter of the sweetener and oat starch is expected to be absorbed in the small intestine of the subject FIG. 1 shows the plots of Δ plasma glucose vs time for three tests described in Table 1 The glucose peak for the 17 g lactose/17 g sucrose sweetener with 16 g starch (curve B) is typically the same intensity and time as that for the 34 g sucrose with 16 g starch control (curve A), but the AUC (1613 mg-min/dL) is significantly less than for sucrose (3155 mg-min/dL). The Δ plasma glucose values for 90 and 120 minutes are different from those of sucrose The subject observed no GI effects at all.

The 8.5 g lactose/17 g sucrose/8.5 g fructose sweetener (curve C) in FIG. 1 showed ½ of the peak plasma glucose increase of sucrose and significantly lower AUC (1002 mg-min/dL) than for sucrose (3155 mg-min/dL). None of the time values was significantly different from sucrose because this formulation showed a different time peak and shape of curve each of the four times it was tested. The subject observed very mild GI rumblings and fullness, which were related to the test article, two out of four times tested. It is interesting to note too that the sucrose curve (A) returned from its peak to the fasting blood glucose level at 3 hours, in contrast to the new sweeteners (curves B and C), which fell to fasting blood glucose levels within 1.5 to 2 hours and stayed below fasting plasma glucose level until some time after 3 hours.

Without wishing to be held to this explanation, we surmise this reduction of plasma glucose below fasting level is related to the fermentation of the sugars to short chain fatty acids (SCFA's) in the colon. Absorption of the two most dominant SCFA's (acetic and propionic acids) from the colon and initial metabolism to triglyceride requires that glucose be oxidized to make ATP.

Example 2

Caloric Values of Mixtures of Lactose, Sucrose, and Fructose

Figure 2:
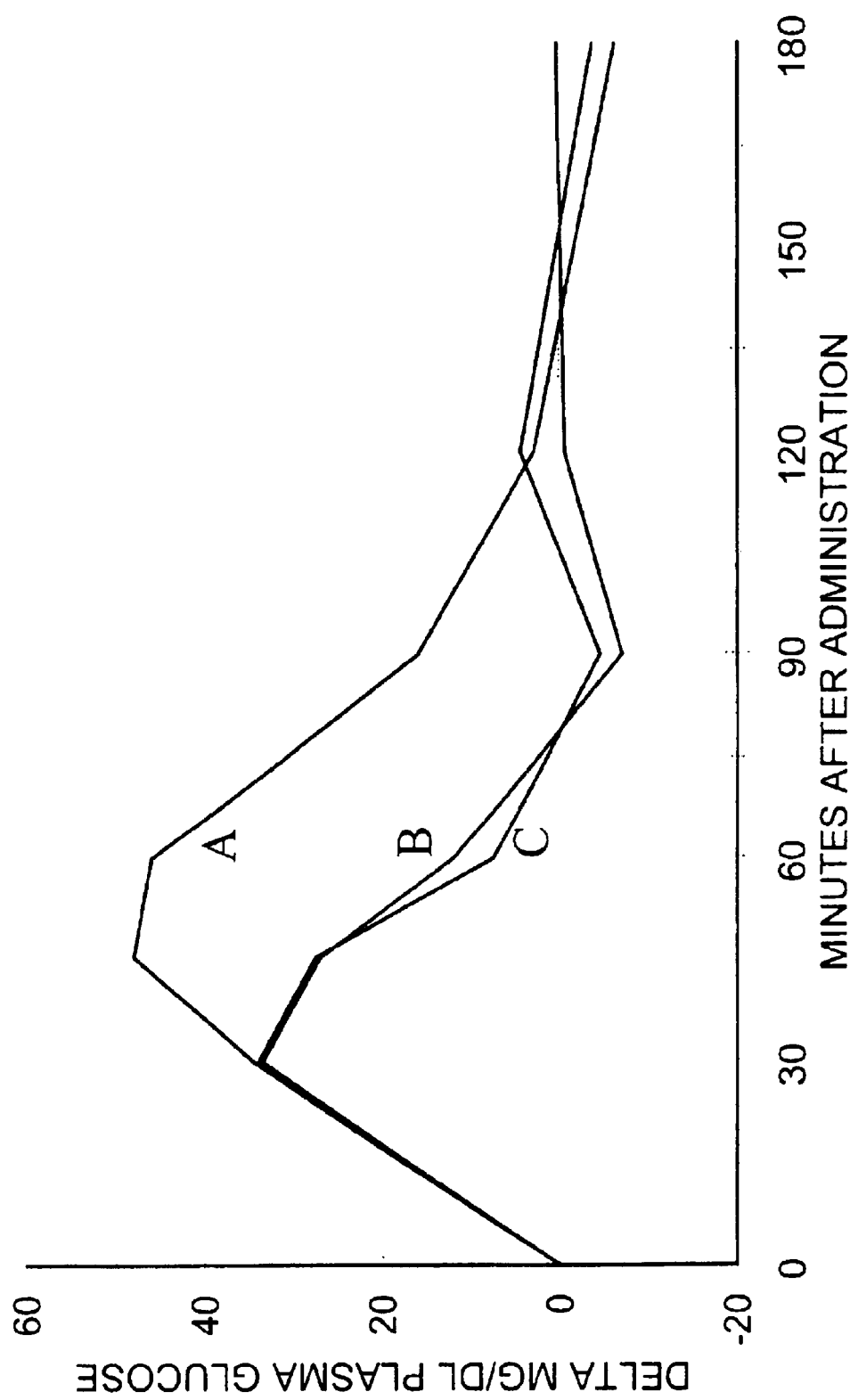
FIG. 2 shows the effects of ingestion of various mixtures of sugars in water on plasma glucose levels.

Test articles were aqueous solutions (in 200 g water) of 50 g of total carbohydrates, which were prepared early in the morning before the test. All of the same protocol criteria were applied for the test, as described in Example 1 above, except that times for blood samples were 0, 30, 45, 60, 90, 120, and 180 minutes. The test subjects were Subject #1, described above, and Subject #2, a 24-year-old, healthy Caucasian male (BMI=27.7 kg/m$^2$). See FIGS. 3 and 2, respectively, for results of their OTT's.

Calculation of estimated caloric value (ECV) demands some explanation here, as the calculation requires acceptance of some reasonable assumptions:

GI values for lactose monohydrate, fructose, sucrose and oat starch are 46, 23, 64, and 100, respectively.

Caloric values for lactose monohydrate, fructose, sucrose and oat starch are 3.8, 3.7, 3.9, and 3.7 kcal/g, respectively.

The order for complete active absorption of sugar mixtures from the small intestine to the bloodstream is fructose>starch (as maltose and α-dextrins) >sucrose>lactose.

Passive absorption of unhydrolyzed disaccharides is assumed to be zero for these calculations.

Disaccharides not actively absorbed pass to the colon, where they are fully degraded by microflora.
    78% of the disaccharides form short chain fatty acids (SCFA's), which are fully absorbed and used by the body with 50%×0.85=42.5% energy efficiency vs glucose (Livesey, Int J Food Sci Nutr, 44, 221–241, 1993).
    22% of the disaccharides are converted to biomass, which is calorically unavailable to the host (Weber et al, J Lab Clin Med, 110, 259–263, 1987).

NB—Starch (not part of the sweetener) which passes to the colon and is degraded microbially subtracts energy value from the sweetener, a component of which (lactose) caused it to pass to the colon.

The accepted caloric value of a sweetener for nutrition labeling purposes may require consideration of the disposition of the sweetener components alone, and not the effect the sweetener has on disposition of other nutrients. So, the following tests of claimed mixtures of the sugars in aqueous solutions, without other nutrients, serve to demonstrate the most conservative estimated caloric values (ECV's) of the sweetener.

Figure 3:
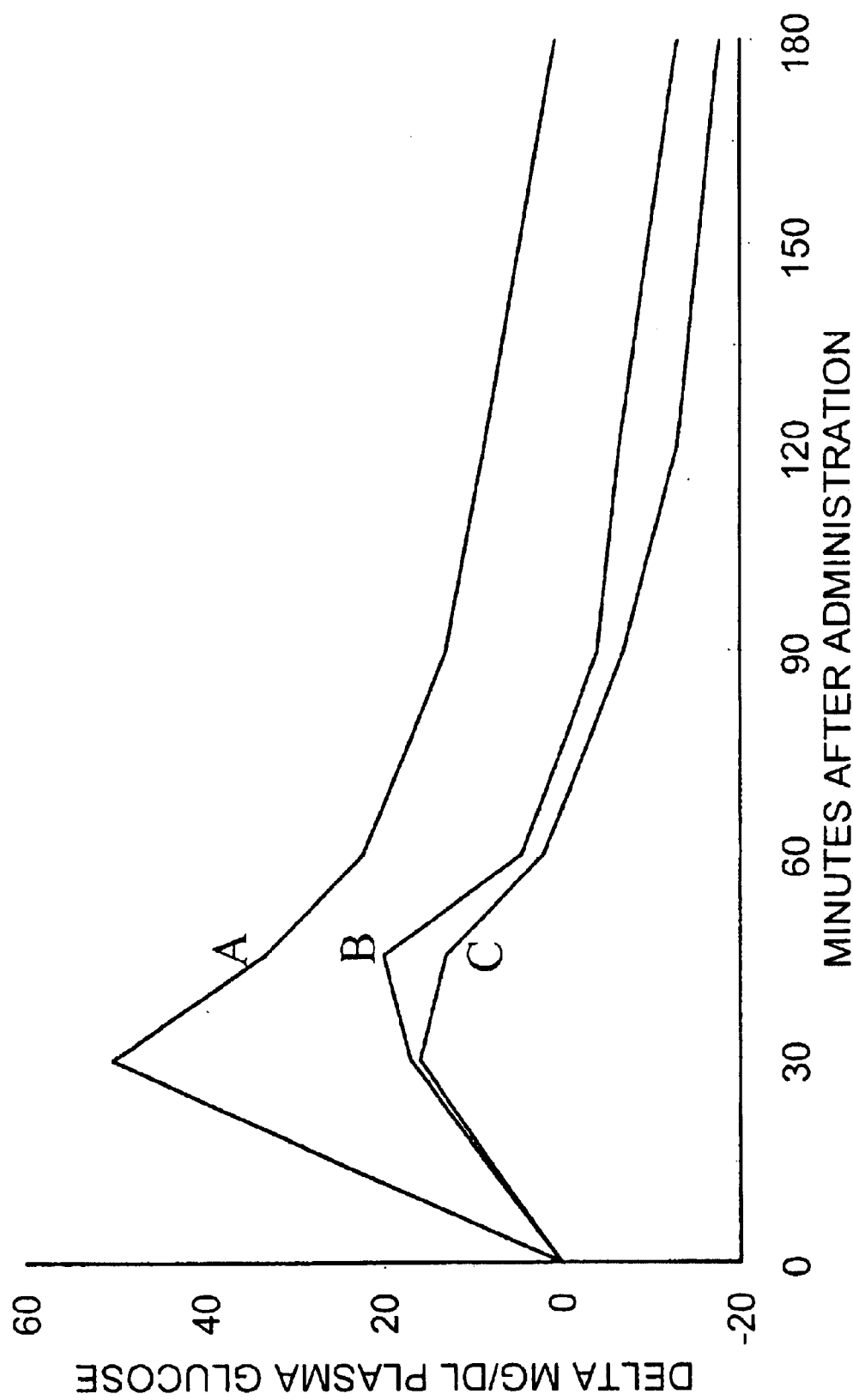
FIG. 3 shows the effects of ingestion of various mixtures of sugars in water on plasma glucose levels.

In FIG. 3, a 50-g sucrose in 200-g water solution (curve A, where N=3 tests) was used as the control (defined as 3.9 kcal/g) for a 20% aqueous solution of 16 g lactose/17 g sucrose/17 g fructose in normal Subject #1 (curve B, where N=3 tests) Plasma glucose increments were significantly lower for the mixture of sugars at 30, 60, and 90 minutes, as well as the AUC (754 mg-min/dL vs 2935 mg-min/dL). The subject noted slight rumblings and fullness in the GI tract from 1.7 hours on. The estimated caloric value (ECV) for the sugar mixture was 2.2 kcal/g.

For the sugar mixture, 12.5 g lactose/25 g sucrose/12.5 g fructose in 20% aqueous solution (curve C, where N=3 tests), plasma glucose increments were significantly lower for the mixture of sugars at 45 and 90 minutes, as well as the AUC vs sucrose (580 mg-min/dL vs 2935 mg-min/dL). Two of three times, the subject noted slight GI rumblings at two different times; once, there were no GI effects. The estimated caloric value (ECV) for the sugar mixture was calculated as 1.9 kcal/g. When the same ratio of the three sugars (total 34 g) was added to oat starch (16 g) for an OTT in the same subject (see FIG. 1, curve C, test of 8.5 g lactose/17 g sucrose/8.5 g sucrose/16 g starch, where N=4 tests), the ECV for the sweetener was 1.0 kca/g. Clearly, the sugars of the sweetener interfere with absorption of a fraction of the starch from the oats In FIG. 2, a 50-g sucrose in 200-g water solution (curve A, where N=2 tests) was used as the control for a 20% aqueous solution of 20 g lactose/30 g sucrose in the normal Subject #2 (curve B, where N=2 tests). Plasma glucose increments were significantly lower for the mixture of lactose and sucrose at 90 minutes. The ECV for the two-sugar mixture was calculated as 2.1 kcal/g. When 7 g fructose replaced an equal amount of sucrose in the previous test (curve C, where N=2 tests), plasma glucose increments were significantly lower for the mixture of sugars at 60 minutes vs sucrose. No gastrointestinal effects were observed. The ECV for the three-sugar mixture (20 g lactose/23 g sucrose/7 g fructose) was calculated as 2.4 kcal/g. The shapes of both curves for the mixed sugars are interesting because the initial rate of glucose absorption (0 to 30 minutes) is the same for the two test articles as for the sucrose control.

Without wishing to be held to this explanation, we believe this identical initial rate of glucose absorption occurs because inhibition of lactose, and therefore sucrose and starch, absorption does not work well until a certain level of fructose accumulates in the lumen of the small intestine. There is consequently a caloric advantage to having a minimal amount of fructose ingested as part of the sweetener, rather than waiting for sucrose to hydrolyze and supply the threshold fructose concentration in the small intestine.

Example 3

Use of New Sweetener by Impaired Glucose Tolerant Subject

Figure 4:
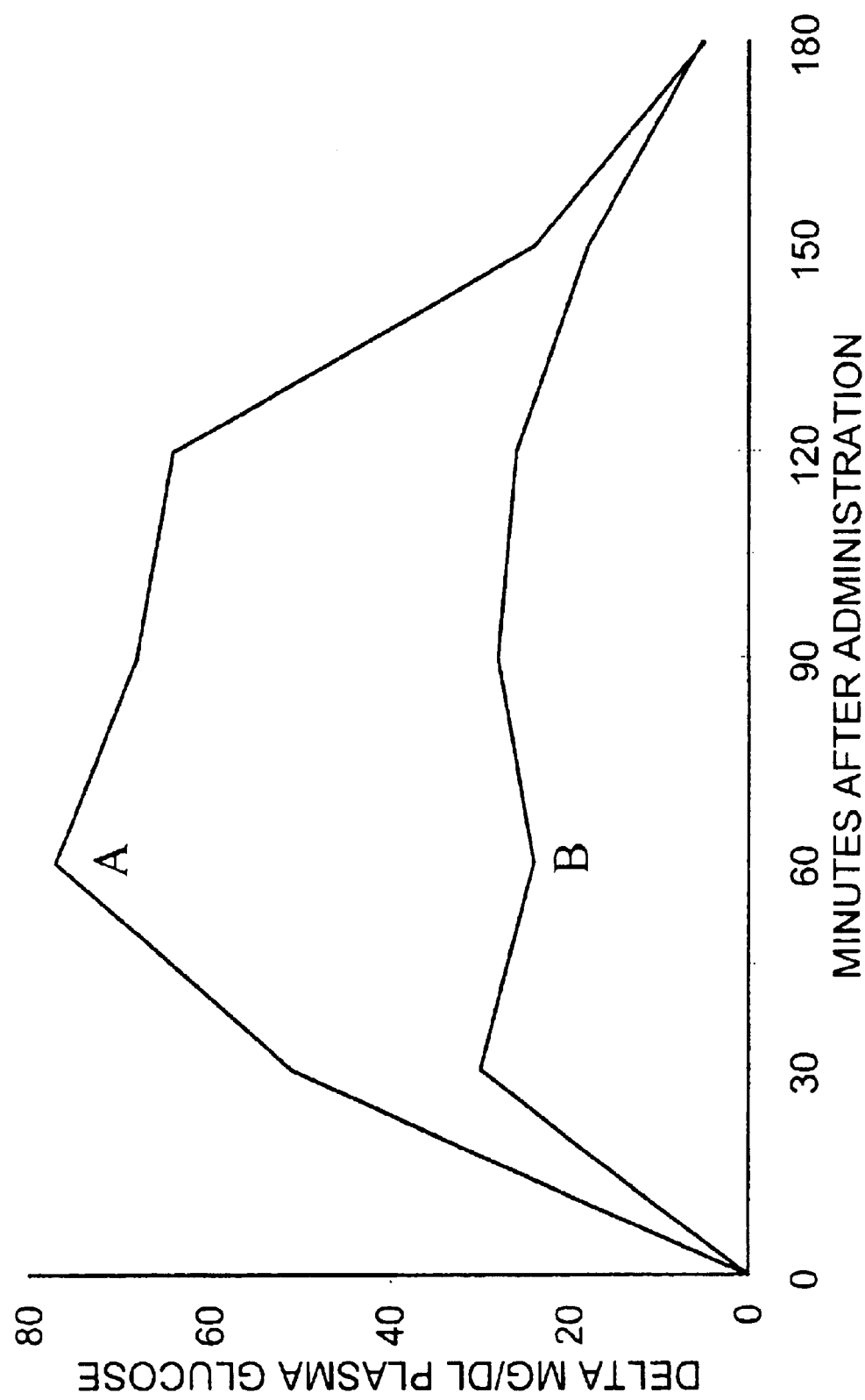
FIG. 4 shows the effects of ingestion of various mixtures of sugars in oatmeal by a person with impaired glucose tolerance on plasma glucose levels.

The test subject with impaired glucose tolerance (IGT) was an 84-year-old Caucasian male (BMI=21.5 kg/m$^2$) in relatively good health. His daily drug regimen included Coumadin® and Cardoxin®, all taken after OTT. The same OTT protocol for Example 1 was used for the IGT subject See FIG. 4 for IGT's OTT results.

IGT showed a peak plasma glucose increase at 30 minutes for the 20 g lactose/14 g sucrose/16 g starch test article (curve B) that was 39% of the peak from 34 g sucrose/16 g starch (curve A) His plasma glucose concentration remained nearly constant for ~1.5 hours after peaking, then dropped back to nearly baseline by 3 hours. The subject felt no GI effects. Unlike the sucrose/starch control (curve A), the lactose/sucrose/starch test article(curve B) never caused his plasma glucose level to break above 200 mg/dL, an important criterion for diabetes (especially at 2 hours) The AUC for the sucrose/lactose/starch dose was 45% of the AUC for sucrose/starch (3860 mg-min/dL vs 8595 mg-min/dL). Maintenance of low postprandial AUC is important for keeping control of glycosylated hemoglobin in type 2 pre-diabetics and diabetics, as is controlling caloric intake in most cases. Caloric value of the sweetener added to the oatmeal for the lactose/sucrose case was reduced from 3.9 kcal/g for sucrose to 1.0 kcal/g.

Example 4

Use of New Sweetener by Type 2 Diabetic

Figure 5:
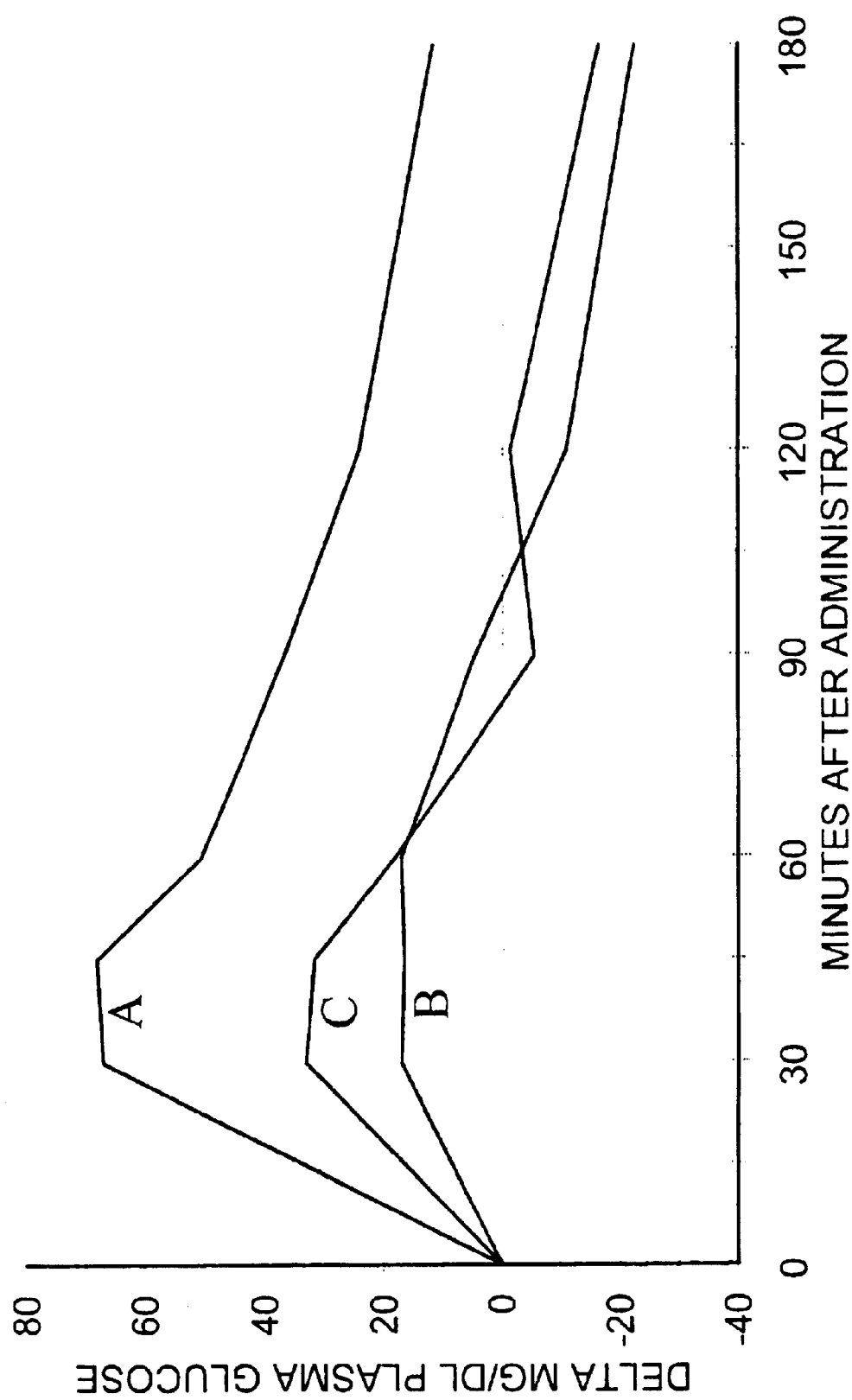
FIG. 5 shows the effects of ingestion of various mixtures of sugars in water by a person with diabetes on plasma glucose levels.

The type 2 diabetic subject (DM2) was a 51-year-old Caucasian female (BMI=32.8 kg/M$^2$), who was trying to control her diabetes without insulin or oral medications. Her daily drug regimen included Premarin®, Prempro®, Xenical®, and Lipitor®, all taken after OTT was completed each day. The same OTT protocol for Example 2 was used for DM2, except that 100 g water was used for the test solution. DM2 was tested with duplicate 50, 25, and 15 g sucrose OTT's to assure linearity of the plasma glucose response as AUC vs dose. The dose response was linear between 0 and 25 g sucrose; thus all subsequent testing with this subject was done with 25 g total carbohydrate. See FIG. 5 for DM2's OTT results.

The 25-g sucrose control (curve A, where N=2 tests) showed an unexpectedly large plasma glucose rise with a peak at 45 minutes. The mean plasma glucose level for 30 and 45 minutes broke above 200 mg/dL, and the AUC was large for a relatively small dose of sucrose Dosing with 25 g of 1:3 lactose/fructose (curve B, where N=2 tests) showed significantly reduced Δ plasma glucose levels at 30, 45 and 60 minutes and a reduced AUC vs sucrose control (1113 mg-min/dL vs 6184 mg-min/dL). With 1:3 lactose/fructose, the plasma glucose level never broke above 200 mg/dL, even though the fasting blood glucose level at time 0 for the 1:3 lactose/fructose test was 42 mg/dL higher than that for sucrose. The subject felt no GI effects Because of the low peak glucose concentration and AUC, 1:3 lactose/fructose has significant potential for use by diabetics. The ECV for the sweetener is 2.3 kcal/g.

Dosing with 25 g of 2.3.3 lactose/sucrose/fructose (curve C, where N=2 tests) showed significantly reduced Δ plasma glucose levels at 30, 60, and 120 minutes and a reduced AUC vs sucrose control (1448 mg-min/dL vs 6184 mg-min/dL). The subject observed no GI effects. The ECV for the sweetener is 2.2 kcal/g.

Example 5

Paired-Comparison Test for Sweetness

Six adult subjects (3 males, 3 females) served as tasters for the claimed described sugar mixtures as 10 wt % aqueous solutions at ambient temperature. The study was a blind paired-comparison taste study to evaluate relative sweetness of six sugar mixtures vs each of the 0, 4, 8, 12, 16, or 20 wt % aqueous sucrose solutions, used as standards. Each subject tested each unknown twice. The mean results as percent sucrose equivalent (%SE) are presented in Table 2

TABLE 2

| Relative Sweetness | | | |
|---|---|---|---|
| Lactose · H2O (wt %) | Sucrose (wt %) | Fructose (wt %) | % SE |
| 50 | 50 | 0 | 63 |
| 40 | 60 | 0 | 70 |
| 0 | 50 | 50 | 128 |
| 37.5 | 25 | 375 | 86 |
| 25 | 0 | 75 | 94 |
| 25 | 50 | 25 | 96 |

Example 6

Preparation of Soft Drink Mix

A package of grape-flavored Kool-Aid® unsweetened soft drink mix (3.9 g net weight) was mixed with 1 cup of sugar (215 g) in 2 quarts of cool tap water (Drink B). A second drink was prepared by replacing the sugar in the first recipe with 1 cup of dry mixture (210 g) of 25 wt % lactose monohydrate, 50 wt % sucrose, and 25 wt % fructose (Drink A). The two drinks were refrigerated for at least 2 hours before taste-testing by eight individuals. Four of eight untrained tasters rated B sweeter than A. All agreed the comparison was extremely close. Five of eight of the same tasters, basing their decision on taste only, said they would buy A over B. Five thought that A was prepared from table sugar as the only sweetener, and three thought B was prepared from table sugar only. The estimated caloric values of an 8-oz serving were 105 kcal for B and 50 kcal for A, a reduction in caloric value of 52%.

Example 7

Preparation of Instant Quaker Oats®

Two samples of sweetened oatmeal were prepared. The first used 34 g light brown cane sugar and one pack (28 g) of Instant Quaker Oatmeal in a bowl. Water (½ cup) was added, the mixture stirred, and heated for 1 minute at the high setting of a microwave oven, stirred briefly, and heated for another 30 seconds. The second preparation used a mixture of 8.5 g lactose monohydrate/17 g dark brown cane sugar/8.5 g fructose in place of the light brown cane sugar in the first preparation. The colors of the two sweeteners were nearly the same. The taste and texture for the two oatmeal preparations were both the same. The estimated caloric values were 233 and 134 kcal, respectively, a reduction in caloric value of 42%.

Example 8

Preparation of Sugar Cookies

A Ingredients

| | |
|---|---|
| ½ cup granulated sugar (107.5 g × 3.9 kcal/g) | 1 teaspoon baking soda |
| ½ cup brown sugar | 2 teaspoons cream of tartar (14 kcal) |
| 1 egg (44 g, 70 kcal) | 1 teaspoon vanilla |
| 1 cup shortening (179 g × 9.2 kcal/g) | ¼ teaspoon salt |
| 2 cups flour (280 g × 3.7 kcal/g) | |

Mix all ingredients and chill dough in refrigerator. Roll dough in balls and dip in granulated sugar. Bake in a medium oven at 350° F. for 12 minutes. Let cookies (N≈45) cool before eating.

B Ingredients

| | |
|---|---|
| 2 ounces Krystar 300 (fructose) | 2 cups flour |
| 2 ounces lactose monohydrate | 1 teaspoon baking soda |
| ½ cup brown sugar | 2 teaspoons cream of tartar |
| 1 egg | 1 teaspoon vanilla |
| 1 cup shortening | ¼ teaspoon salt |

Mix all ingredients and chill dough in refrigerator. Roll dough in balls and dip in a mixture of 25 wt % Krystar 300/50 wt % granulated sugar/25 wt % lactose monohydrate. Bake in a medium oven at 350° F. for 10 minutes Let cookies (N≈45) cool before eating.

The two recipes, A and B, were executed as described. Six people ate cookies A and B and agreed that the taste of each was nearly identical. The B recipe cookies were a slightly darker color on top than the A cookies. Each cookie contained 29 wt % sugars and 24 wt % fat. The estimated caloric values of the individual cookies A and B were respectively 80 and 66 kcal, a reduction in caloric value of 18%.

We claim:

1. A process of retarding the absorption in the small intestine of ingested sucrose, lactose, and dietary starch by a person with a need to retard carbohydrate absorption comprising:

administering an effective amount of a mixture of sugars comprising in percent by weight of the mixture of sugars: lactose 10 to 80, and either fructose or sucrose or a mixture of fructose and sucrose, 20 to 90, to a person with a need to retard carbohydrate absorption.

2. The process of claim 1 wherein the mixture of sugars are crystalline sugars of similar crystal size, are co-crystallized or spray-dried from an aqueous solution of sugars, are in the form of an aqueous syrup, or are in the form of a solution in a water and alcohol mixture.

3. The process of claim 1, wherein the lactose is in the form of the α-lactose monohydrate or the anhydrous β-anomer.

4. The process of claim 1 wherein the fructose is in the crystalline form or in an aqueous syrup.

5. The process of claim 1 wherein the sucrose is in the granulated crystalline form, cotifectioner's form, brown sugar form, or as molasses.

6. The process of claim 1 wherein the mixture of sugars further comprises food-grade additives and processing aids which keep the mixture dry and flowable.

7. The process of claim 1 wherein the mixture further comprises aspartame, 1,6-dichloro-1,6-dideoxy-β-D-fructofuranosyl-4-chloro-4-deoxy-α-D-galactopyranoside, acesulfame-K, saccharin, stevioside, thaumatin, alitame, and N-[N-(3,3-dimethylbutyl)-L-α-aspartyl]-L-phenylalanine-1-methyl ester.

8. The process of claim 1 wherein the mixture of sugars further comprises a diluent.

9. The process of claim 8 wherein the diluent is a maltodextrin, polydextrose, or cellulose.

10. The process of claim 1 wherein the percentage of weight of lactose is 10 to 80 and the percentage of weight of fructose is 20 to 90.

11. The process of claim 1 wherein the percentage of weight of lactose is 25 to 60 and the percentage of weight of fructose is 40 to 75.

12. The process of claim 1 wherein the percentage of weight of lactose is 10 to 80 and the percentage of weight of sucrose is 20 to 90.

13. The process of claim 1 wherein the percentage of weight of lactose is 25 to 60 and the percentage of weight of sucrose is 40 to 75.

14. The process of claim 1 wherein the percentage of weight of lactose is 24 to 52 and the percentage of weight of sucrose is 24 to 52 and the percentage of weight of fructose is 24 to 52.

15. A process of retarding the absorption in the small intestine of ingested sucrose, lactose, and dietary starch by a person with a need to retard carbohydrate absorption consisting of:

administering an effective amount of a mixture of sugars comprising in percent by weight of the mixture of sugars: lactose 10 to 80, and either fructose or sucrose or a mixture of fructose and sucrose, 20 to 90, to a person with a need to retard carbohydrate absorption.

16. The process of claim 1 wherein the person with a need to retard carbohydrate absorption is a person with a need to control postprandial blood glucose levels.

17. The process of claim 1 wherein the person with a need to retard carbohydrate absorption is a person with a need to control glycosylated hemoglobin levels.

18. The process of claim 1 wherein the person with a need to retard carbohydrate absorption is a person with a need to maintain a healthy population of intestinal microbes.

19. The process of claim 1 wherein the person with a need to retard carbohydrate absorption is a person with a need to encourage the growth of beneficial bacteria in the colon.

* * * * *